US011674928B2

(12) United States Patent
Papadakis et al.

(10) Patent No.: US 11,674,928 B2
(45) Date of Patent: Jun. 13, 2023

(54) DETECTING NUCLEIC ACIDS IN IMPURE SAMPLES WITH AN ACOUSTIC WAVE SENSOR

(71) Applicant: Foundation for Research and Technology Hellas, Heraklion (GR)

(72) Inventors: Georgios Papadakis, Heraklion (GR); Electra Gizeli, Heraklion (GR)

(73) Assignee: Foundation for Research and Technology Hellas, Heraklion (GR)

( * ) Notice: Subject to any disclaimer, the term of this patent is extended or adjusted under 35 U.S.C. 154(b) by 415 days.

(21) Appl. No.: 16/010,617

(22) Filed: Jun. 18, 2018

(65) Prior Publication Data

US 2019/0011401 A1     Jan. 10, 2019

(30) Foreign Application Priority Data

Jun. 16, 2017 (GB) ..................... 1709659

(51) Int. Cl.
| | | |
|---|---|---|
| *C12Q 1/6825* | (2018.01) | |
| *C12Q 1/6844* | (2018.01) | |
| *C12Q 1/6806* | (2018.01) | |
| *C12Q 1/6853* | (2018.01) | |
| *G01N 29/032* | (2006.01) | |
| *G01N 33/02* | (2006.01) | |
| *G01N 33/487* | (2006.01) | |

(52) U.S. Cl.
CPC ......... *G01N 29/032* (2013.01); *C12Q 1/6806* (2013.01); *C12Q 1/6825* (2013.01); *C12Q 1/6844* (2013.01); *C12Q 1/6853* (2013.01); *G01N 33/02* (2013.01); *G01N 33/487* (2013.01); *G01N 2291/022* (2013.01); *G01N 2291/02809* (2013.01)

(58) Field of Classification Search
CPC ............ C12Q 2565/634; C12Q 1/6806; C12Q 1/6825; C12Q 1/6844; C12Q 1/6853; G01N 29/032; G01N 2291/022; G01N 2291/02809; G01N 33/487
See application file for complete search history.

(56) References Cited

U.S. PATENT DOCUMENTS

2006/0051248 A1* 3/2006 Cho .................. B01L 3/502715
                                                            422/400

FOREIGN PATENT DOCUMENTS

| WO | WO-0068419 A2 * | 11/2000 | ........... G01N 29/022 |
| WO | 200814513 A1 | 12/2008 | |
| WO | 2009005542 A2 | 1/2009 | |
| WO | 2013033049 A1 | 3/2013 | |
| WO | 2017005663 A1 | 1/2017 | |
| WO | WO-2017005663 A1 * | 1/2017 | ........... C12Q 1/6825 |

OTHER PUBLICATIONS

Papadakis et al., "Optimized acoustic biochip integrated with microfluidics for biomarkers detection in molecular diagnostics," Biomed. Microdevices, Mar. 29, vol. 19, No. 16, pp. 1-11. (Year: 2017).*
Papadakis et al., Biomed. Microdevices, published on-line Mar. 29, vol. 19, No. 16, pp. 1-11 (Year: 2017).*
Papadakis, G., et al., Acoustic Detection of DNA Conformation in Genetic Assays Combined with PCR, Scientific Reports, Jun. 19, 2013, pp. 1-8, 3 : 2033, Nature Publishing Group, London, GB.
Papadakis, G., et al., Bacteria Murmur: Application of an Acoustic Biosensor for Plant Pathogen Detection, PLOS One, Jul. 15, 2015, pp. 1-11, 10 : 1371, PLOS, San Francisco, US.
Shen, Y., et al., Influence of Solution Chemistry on the Deposition and Detachment Kinetics of RNA on Silica Surfaces, Colloids and Surfaces B: Biointerfaces, Oct. 8, 2010, pp. 443-449, 82, Elsevier, Amsterdam, NL.
Papadakis, G., et al., Optimized Acoustic Biochip Integrated with Microtluidics for Biomarkers Detection in Molecular Diagnostics, Biomed Microdevices, Mar. 29, 2017, pp. 1-11, 19, Springer Science+ Business Media, Berlin/Heidelberg, DE.
Kordas, Antonis, et al., Rapid Salmonella Detection Using an Acoustic Wave Combined with the RCA Isothermal DNA Amplification Method, Sensing and Bio-Sensing Research, Oct. 12, 2016, pp. 121-127,11, Elsevier B.V., Amsterdam, NL.
Tsortos, Achilleas, et al., On the Hydrodynamic Nature of DNA Acoustic Sensing, Analytical Chemistry, May 27, 2016, ACS Publications, Washington, US.
Yao, Chunyan, et al., Sensitive and Specific HBV Genomic DNA Detection Using RCA-Based QCM Biosensor, Sensors and Acuators B: Chemical, Feb. 4, 2013, pp. 382-387, 181, Elsevier B.V., Amsterdam, NL.
Prakrankamanant, Preeda, et al., The Development of DNA-Based Quartz Crystal Microbalance Integrated with Isothermal DNA Amplification System for Human Papillomavirus Type 58 Detection, Biosensors and Bioelectronics, Aug. 17, 2012, pp. 252-257, 40, Elsevier B.V., Amsterdam, NL.

* cited by examiner

Primary Examiner — Young J Kim
(74) Attorney, Agent, or Firm — Kearney McWilliams Davis; Erik J. Osterrieder

(57) ABSTRACT

An acoustic sensor detects binding of a nucleic acid analyte in an impure liquid sample by measurement of the energy of the acoustic wave resulting from the binding of the nucleic acid target to the sensor surface. The analysis may be preceded by carrying out a nucleic acid amplification procedure in situ on a crude or impure biological sample and the analysis is tolerant of the presence of reagents or by-products of the amplification procedure, and also materials present from the initial biological sample.

19 Claims, 6 Drawing Sheets

Specification includes a Sequence Listing.

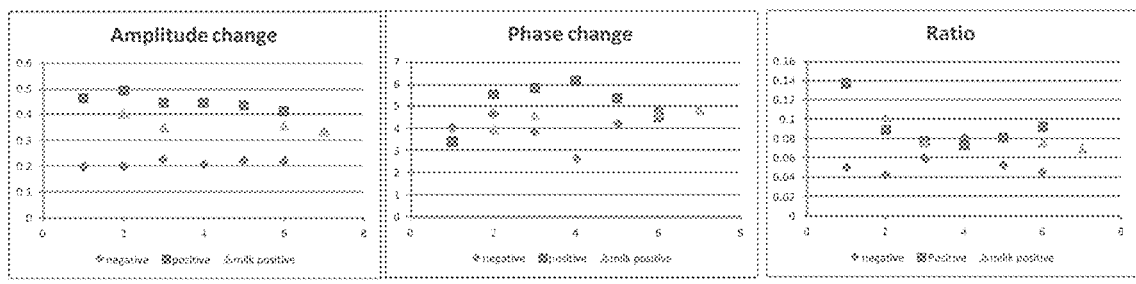
Fig. 7A   300   Fig. 7B   Fig. 7C

SEQUENCE LISTING

```
<160> NUMBER OF SEQ ID NOS: 10

<210> SEQ ID NO 1
<211> LENGTH: 19
<212> TYPE: DNA
<213> ORGANISM: Salmonella typhimurium
<220> FEATURE:
<223> OTHER INFORMATION: Forward primer for 635bp DNA

<400> SEQUENCE: 1
gacacctcaa aagcagcgt                                                19

<210> SEQ ID NO 2
<211> LENGTH: 19
<212> TYPE: DNA
<213> ORGANISM: Salmonella typhimurium
<220> FEATURE:
<223> OTHER INFORMATION: Reverse primer for 635bp

<400> SEQUENCE: 2
agacggcgat acccagcgg                                                19

<210> SEQ ID NO 3
<211> LENGTH: 30
<212> TYPE: DNA
<213> ORGANISM: Salmonella typhimurium
<220> FEATURE:
<223> OTHER INFORMATION: Forward primer for 195bp fragment

<400> SEQUENCE: 3
ggatcactaa gctgtggatt acctattatc                                    30

<210> SEQ ID NO 4
<211> LENGTH: 30
<212> TYPE: DNA
<213> ORGANISM: Salmonella typhimurium
<220> FEATURE:
<223> OTHER INFORMATION: Reverse primer for 195bp fragment

<400> SEQUENCE: 4
ctgttatttc ctgcgtggat atttctttag                                    30

<210> SEQ ID NO 5
<211> LENGTH: 18
<212> TYPE: DNA
<213> ORGANISM: Salmonella typhimurium
<220> FEATURE:
<223> OTHER INFORMATION: Primer F3

<400> SEQUENCE: 5
cggcccgatt ttctctgg                                                 18

<210> SEQ ID NO 6
<211> LENGTH: 18
<212> TYPE: DNA
<213> ORGANISM: Salmonella typhimurium
<220> FEATURE:
<223> OTHER INFORMATION: Primer B3

<400> SEQUENCE: 6
```

```
cggcaatagc gtcacctt                                                   18

<210> SEQ ID NO 7
<211> LENGTH: 40
<212> TYPE: DNA
<213> ORGANISM: Salmonella typhimurium
<220> FEATURE:
<223> OTHER INFORMATION: Primer FIP

<400> SEQUENCE: 7
gcgcggcatc cgcatcaata tgcccggtaa acagatgagt                            40

<210> SEQ ID NO 8
<211> LENGTH: 38
<212> TYPE: DNA
<213> ORGANISM: Salmonella typhimurium
<220> FEATURE:
<223> OTHER INFORMATION: Primer BIP

<400> SEQUENCE: 8
gcgaacggcg aagcgtactg tcgcaccgtc aaaggaac                              38

<210> SEQ ID NO 9
<211> LENGTH: 21
<212> TYPE: DNA
<213> ORGANISM: Salmonella typhimurium
<220> FEATURE:
<223> OTHER INFORMATION: Primer Loop-F

<400> SEQUENCE: 9
ggccttcaaa tcggcatcaa t                                               21

<210> SEQ ID NO 10
<211> LENGTH: 22
<212> TYPE: DNA
<213> ORGANISM: Salmonella typhimurium
<220> FEATURE:
<223> OTHER INFORMATION: Primer Loop-B

<400> SEQUENCE: 10
gaaagggaaa gccagcttta cg                                              22
```

DETECTING NUCLEIC ACIDS IN IMPURE SAMPLES WITH AN ACOUSTIC WAVE SENSOR

REFERENCE TO RELATED APPLICATION

The present application claims priority to United Kingdom patent application GB1709659.5 filed on Jun. 16, 2017 and having the same title as the instant application, wherein this priority application is incorporated in its entirety by this reference.

FIELD OF THE INVENTION

The invention relates to the field of measuring the presence or amount of a nucleic acid in an impure sample using an acoustic wave sensor.

BACKGROUND TO THE INVENTION

Current trends for the detection of nucleic acid (NA) biomarker at the point-of-care (POC) focus on the need for developing simple, fast, cost-effective and generic methods.

It is known to provide biosensors with acoustic wave devices as the detection element in combination with a specific biorecognition surface, such as a single stranded DNA probe, which binds the target NA, normally through hybridization. In such devices, the mass of the bound NA is detected from a change in the frequency, phase or velocity of the acoustic wave.

In addition, it is known to combine NA detection with a NA amplification step, the later taking place through an enzymatic amplification procedure, such as PCR or isothermal amplification (Lamp, HDA, RCA etc.), or to use a non-enzymatic amplification method (such as LCR, HCR, etc.).

Irrespective of the sensing device which is used, it is common to first extract an analyte NA from the crude sample and then perform amplification of the purified analyte. Furthermore, after amplification, the product NA is in a complex liquid which contains, in addition to large numbers of the NA, high concentrations of reagents, such as primers, enzymes, glycerol, detergent and also reaction by-products. At the present time, this solution is not brought in contact with the device surface since this would result in a high degree of non-specific binding. Instead, the NA is first purified from the complex solution using an appropriate method (e.g., a spin-column) and then applied on the sensor surface in the working buffer. Furthermore, binding of non-specific components of the liquid product of amplification to the sensing surface is minimised by the use of a sensor surface which supresses the binding of molecules other than the NA target.

For example, an acoustic wave device was used to detect a NA target, from the change in frequency of an acoustic wave arising from the mass of amplified NA bound specifically to the sensing surface in Sens Act B, 2013, 181: 382 (target: HBV genomic DNA) and Bios Bioel. 2013, 40:252 (target: human papillomavirus type 58). In another approach, isothermally produced Salmonella DNA (Sensing Bio-Sensing Research, 2016, 11:121) was detected by measuring the acoustic ratio of the change in the dissipation of energy by the acoustic waves ($\Delta D$) over the corresponding change in the frequency ($\Delta F$). In all the above cases, purified DNA was used as the starting material.

The invention seeks to provide a rapid and reliable analytic test capable of detecting a NA target in an impure liquid sample, for example a sample containing reagents for or products of a NA amplification procedure and/or biological molecules or other contaminants from a crude biological sample. Some embodiments of the invention seek to provide a test device with integrated NA amplification.

Although the invention will be discussed further with reference to the measurement of analytes using a QCM and a Love wave device, the invention may be performed using other types of liquid medium acoustic wave sensor. By a liquid medium acoustic wave sensor we mean an acoustic wave sensor which supports an acoustic wave than can propagate when the sensing surface of the acoustic wave sensor is in contact with a liquid in use.

Within this specification and the appended claims, we use the term nucleic acid (NA) target to refer to the NA which is to be detected by the acoustic sensor. By the analyte we refer to the chemical species which an assay intends to detect in a starting sample. Typically, the NA target is the analyte, however in some embodiments the NA which binds to the sensing surface is different to the analyte in at least some way. The impure liquid sample is the liquid which is analysed, in contact with the sensing surface of the acoustic sensor, to determine the presence or amount of the analyte (if any) in the impure liquid sample.

One skilled in the art will appreciate that the energy losses of an acoustic wave generated by an acoustic wave sensor may be measured by measuring the amplitude or dissipation or resistance, or any other parameter related to the energy of the acoustic wave and could reflect changes of the viscoelastic properties at the device/liquid interface or changes of the intrinsic viscosity of surface bound bio-entities (i.e., biomolecules or nanoparticles). On the other hand, the frequency and phase, are, for example, affected by mass deposited on the sensing surface of the acoustic wave sensor. Where we refer to the acoustic ratio we refer to the ratio of the change in dissipation (D) or amplitude (A) of the acoustic wave to the change in frequency (F) or phase (Ph), respectively, of the acoustic wave arising from binding to the sensing surface of nucleic acid (where present) and other materials, for example $\Delta D/\Delta F$, the ratio of the change in dissipation to the change in frequency.

Within this specification and the appended claims, references to nucleic acids (e.g. RNA, DNA and other polymers of nucleotides) are intended to include both natural macromolecules and synthetic variants, such as NAs including non-natural bases etc. and in some embodiments the NAs have specific binding moieties (e.g. are biotinylated). The term "nucleic acid" (NA) is not intended to imply any specific minimum number of nucleotides or base pairs, although NAs detected according to the invention typically have at least 20 nucleotides or base pairs.

SUMMARY OF THE INVENTION

According to a first aspect of the present invention there is provided a method of measuring a nucleic acid (NA) target in an impure liquid sample, the method comprising providing an acoustic wave sensor having a sensing surface, generating an acoustic wave in the impure liquid sample through the sensing surface while the impure liquid sample is in contact with the sensing surface, measuring the energy loss of the acoustic wave, and comparing the measured energy loss with a reference to thereby determine the presence or amount of the nucleic acid target.

We have found that by measuring the change in the energy losses of the acoustic wave which arise when NA (where present) in the impure liquid sample binds to the sensing surface, it is possible to reliably detect a NA despite the presence of impurities which may bind to the sensing surface and increase the mass loading of the sensing surface. This contrasts with mass-sensitive measurements based on the frequency, phase or velocity of an acoustic wave which can be strongly affected by the presence of non-specifically binding material.

The energy losses are typically reflected in the amplitude or dissipation of the acoustic wave or electrical resistance changes. The presence or amount of the NA target may be determined from the difference between the measured energy loss and a reference (e.g. in comparison to a measurement of energy loss before the impure liquid sample was brought into contact with the sensing surface, or a measurement of energy loss of an acoustic wave in corresponding apparatus with a control sample or a predetermined stored reference value). The method may comprise bringing the impure liquid sample into contact with the sensing surface.

The impure liquid sample in contact with the sensing surface may be or comprise a crude sample, for example a sample of a body fluid (blood, urine, sputum etc.), a food sample (milk, fruit juice etc.) and/or a sample from the environment (sea water, lake water etc.), all of which may contain in addition to the analyte, other biomolecules such as proteins, or carbohydrates, or fatty acids, or other chemicals and and/or cells. The crude sample may be diluted in diluent. In another case, the impure liquid sample can be a sample comprising whole or lysed cells. Impure liquid samples may also comprise any of the above together with reagents for procedures carried out before detection with the acoustic sensor, for example reagents for a NA amplification (detergent, primers, enzymes, glycerol, etc.), or for cell culture (cell growing medium) etc. It may be that the NA is detected in an impure sample which comprises components other than the target NA which bind to the sensing surface and thereby change the frequency or phase of the acoustic wave significantly, e.g. by at least 10%.

The target NA may be the analyte in which case it may be that the method does not include a NA amplification step. However, it may be that the target NA is produced via an amplification process, which might be carried out in the presence of the initial impure sample where the analyte was present, and may be either an identical copy of the initial analyte or slightly modified, for example through the addition of a tag molecule (biotin, cholesterol etc.). In the latter case, where the NA target is different to the analyte, the NA target might be modified from the actual analyte, e.g. a subset of the nucleotide sequence of the analyte or the target nucleic acid could be a label for an assay (e.g. immunoassay) for the analyte, or generated from e.g. the bio bar code type labelling approach. The addition of the amplified NA target to the device surface may occur directly after the amplification process and without any further NA purification step. In some embodiments, formation of the NA target (e.g. by amplification) may take place in an impure liquid sample which is already in contact with the sensing surface. In this case, the reference may be measured energy losses before or during the formation (e.g. amplification) of the NA target.

In the present invention, the sensing surface typically also comprises a layer for target NA binding, designed so that it does not necessarily supress non-specific binding and for this reason, resulting in both target NA and non-specific binding. The layer employed on the sensing surface should be able to bind the target NA through either a specific or non-specific interaction. An example of the former is a neutravidin modified sensing surface which can bind specifically a biotinylated NA target (produced via amplification of the analyte), while an example of the latter is a positively charged polymeric (i.e., polylisine, polyornithine, polybrene, polyethyleneimine etc.) or other bio-chemical (i.e. histone) layer. Thus, the sensing surface may have a cationic layer, typically a cationic polymeric or bio-chemical layer. The sensing surface may have a NA acid attracting component (such as PLL (poly(L-lysine)) or a polymer of another amine-containing monomer) and a protein repelling component (such as PEG (poly(ethylene glycol)). The layer may comprise a copolymer. The cationic layer may comprise PLL-g-PEG, for example.

In the present invention, the amplification of the NA analyte may take place in a specially designed compartment placed adjacent to the acoustic sensor, which can communicate with the sensing surface via a microfluidic channel. The amplification micro-compartment and fluidic channel that connects it to the acoustic device may be part of a cartridge. In another example, the amplification chamber may be a micro-well created on top of the heating element and connected to the acoustic device via a channel. In this construction, the amplification compartment is placed on the surface of a heating or peltier element. The temperature may be regulated to a constant temperature, may cycle through a plurality of temperatures etc. After amplification, the solution with the NA target flows directly on the acoustic sensor surface without including a DNA extraction or purification step. Binding of the NA target and of the other non-specific components takes place on the device surface, which is pre-modified with a specific layer, i.e., neutravidin in the case of biotinylated NA or a positively charged layer. The cartridge can be formed for example from a disposable plastic material, e.g. using micro-injection, hot embossing, additive printing etc. The integral unit may be a disposable cartridge. In another embodiment, the cartridge has a single compartment for amplification and detection, with both taking place concurrently. In this case, the acoustic device is in contact with the heating element and the acoustic signal measurement may occur at a temperature determined by the amplification reaction.

The acoustic wave sensor may be a Bulk Acoustic Wave type device, such as a Quartz Crystal Microbalance, Thickness Shear Mode Resonator or Thickness Shear Bulk Acoustic Resonator (for example, High Fundamental Frequency QCM (HFF-QCM) or Thickness Shear Film Bulk Acoustic Resonator (TS-FBAR)). In this case, the energy loss of the wave generated by the acoustic wave sensor is measured and/or expressed as dissipation or bandwidth or resistance or impedance.

The acoustic wave sensor may be an acoustic wave sensor which generates a shear wave; such Surface Acoustic Wave type devices can employ interdigitated transducers to generate a shear wave, such as a Love wave, Surface Skimming Bulk Wave, Acoustic Plate Mode, Bleustein-Gulyaev wave, leaky acoustic waves or Surface Transverse Wave. In this case, the amplitude of the surface acoustic wave which is generated is typically measured as amplitude.

The shear acoustic wave sensor may be a non-contact, non-interdigitated-transducer based device such as a device employing an electromagnetically excited shear acoustic wave. The liquid medium acoustic wave sensor may be an acoustic wave sensor using a thin membrane to excite an acoustic wave in a configuration known as Flexural Plate Wave or Lamb wave device.

Further optional features are set out in the dependent claims.

DESCRIPTION OF THE DRAWINGS

An example embodiment of the present invention will now be illustrated with reference to the following Figures in which:

FIGS. 7A, 7B, and 7C show the changes in amplitude, phase and acoustic ratio obtained with a Love wave acoustic device, utilizing a surface similar to that illustrated in FIGS. 1A and 1B (PEG-PLL); discrimination between positive and negative samples is only possible through amplitude measurements.

FIG. 8A is an exploded side view of a base unit (bottom of the figure) and disposable microfluidic cassette (top part of the figure); FIG. 8B is a top view of the base unit without the microfluidic cassette present; FIG. 8C is a top view of a disposable microfluidic cassette; FIG. 8D is a top view of the disposable microfluidic cassette fitted onto the base unit.

DETAILED DESCRIPTION OF EXAMPLE EMBODIMENTS

Example 1—Polymer Layer

Figures 1A, 1B:
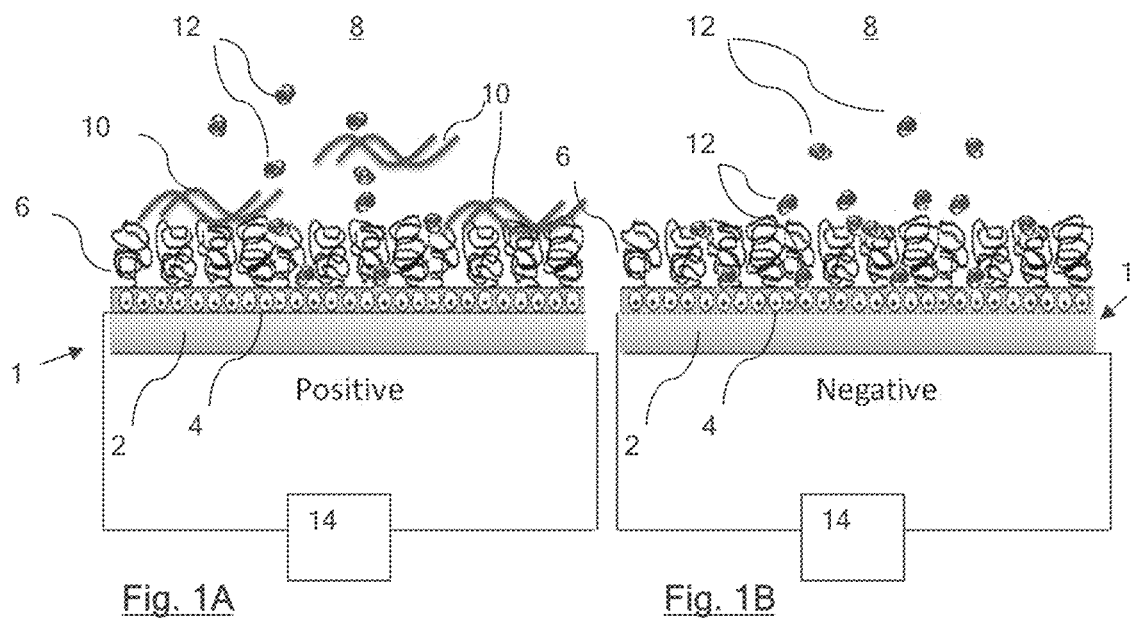
FIG. 1A is a schematic representation of a nucleic acid probe binding to an acoustic sensor sensing surface, along with some non-specific binding components.
FIG. 1B is a schematic representation of a corresponding negative.

With reference to FIGS. 1A and 1B, a QCM acoustic wave device 1 has a substrate 2 having a gold surface 4 with a PEG-PLL co-polymer layer 6 formed thereon. The PEG-PLL co-polymer layer contains a layer of PLL (25)-g-PEG (2) with a layer of PLL (25)-g-PEG(5) thereon and is formed as set out in the experimental example below.

In use, a sample liquid 8, containing both target DNA 10 (in the case of a positive sample such as FIG. 1A, although it is absent in the case of a negative sample such as FIG. 1B) and other components 12, is brought into contact with the polymer layer (functioning as the sensing surface). The target DNA (or other NA analyte) may be amplified using an amplification process or may be detected without any amplification. The other components of the sample liquid include reagents for and/or products of a polymerisation reaction, and/or components from a patient sample, including biomolecules (such as protein, carbohydrates and/or lipids), cell fragments and so forth.

The PEG repels proteins and the PLL binds DNA, however there is still non-specific binding despite the presence of PEG. In the positive sample, the target DNA 10 binds to the sensing surface. In both the positive and negative samples, some of the other components 12 bind to the sensing surface.

An acoustic wave is generated by acoustic wave sensor 14, at a predetermined frequency, and the energy losses of the acoustic wave (in the case of a QCM device, the dissipation) in the presence of the sample liquid is measured. Example operating frequencies are set out in the experimental example below.

The energy loss of the acoustic wave is then compared with a reference value, which may be a measurement of the energy in the presence of a reference liquid, before the sample liquid was brought into contact with the sensing surface; a measurement of the energy loss at a second reference sensor; or a stored reference value. If the energy loss has changed sufficiently relative to the reference value, it is determined that the target DNA is present. In some embodiments, the amount of the target DNA present is estimated qualitatively from the magnitude of the difference between the measured energy and the reference value.

The DNA binds to the surface through electrostatic interactions, independently of nucleic acid sequence, producing a high change in energy loss (e.g. dissipation in the case of a QCM device). We have found that non-specific species that bind, e.g. cell-fragments, PCR-reagents, proteins, fats and carbohydrates present in the impure sample of milk containing lysed cells and cell growing medium bind tightly to the surface, producing a much lower change in energy loss (see FIG. 2B, where the dissipation of the control is much lower than that of the sample with the target NA). This happens even though the amount of non-specifically adsorbed mass is almost the same between the negative and positive samples (see FIG. 2A).

Experimental Results of Example 1: Polymer Layer

First Validation on a QCM

Results shown in FIG. 2, were produced by using the PLL-PEG on a QCM-gold surface depicted in FIG. 1 and as an impure liquid sample (8) milk containing, in the case of the positive sample, both the target DNA 10 (here 635 bp *Salmonella* DNA amplified during PCR) and other components 12 (here cell fragments produced from cell lysis, PCR reagents and polymerization by-products and nutrients from cell culture medium also present in the impure sample, such as proteins, carbohydrates and lipids). In the control experiment the sample 8 was similar to the above with the exception of *Salmonella* DNA which was not included.

When each one of the two samples is brought into contact with the polymer layer (functioning as the sensing surface), the PEG repels the proteins and the PLL binds the DNA; however there is still non-specific binding despite the presence of PEG. In both the positive and negative samples, some of the other components 12 bind to the sensing surface.

Figure 2A:
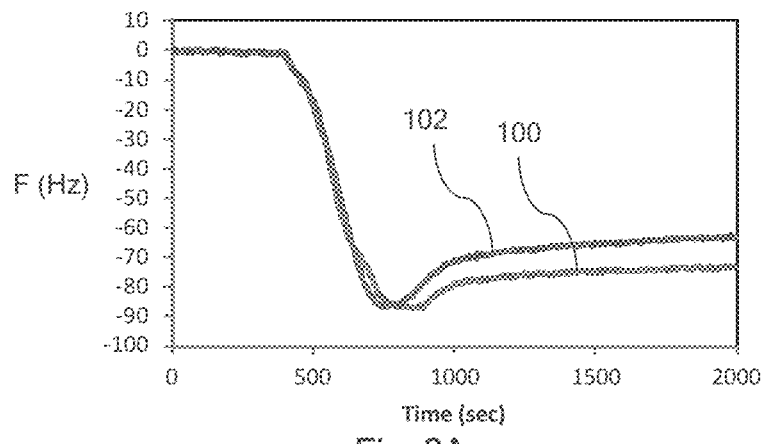
FIGS. 2A and 2B show the changes over time (x-axis) in frequency (F) (FIG. 2A) and dissipation (D) (FIG. 2B), in the presence of positive (100) and negative (102) samples monitored in real-time with a QCM E4 acoustic sensor and using a device surface similar to that illustrated in FIG. 1A positive and FIG. 1B negative, respectively.
Figure 2B:
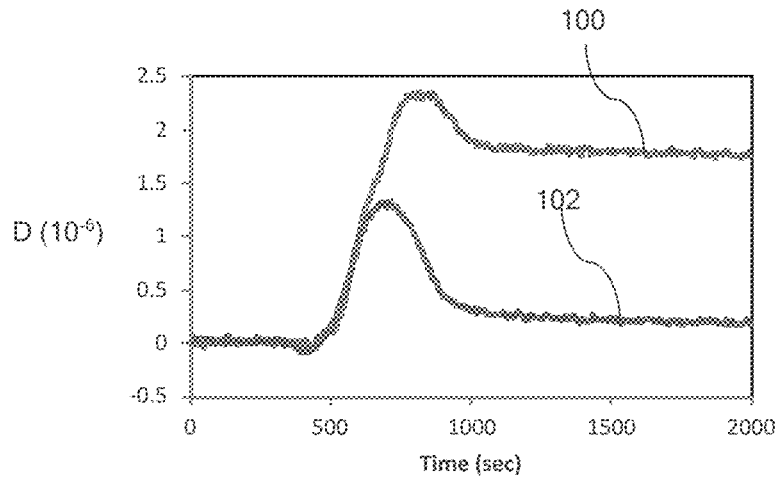

It can be seen from FIG. 2A that there is a significant change in the frequency of the acoustic wave whether or not the target nucleic acid is present. This is as a result of non-specific binding to the sensing surface, which is inherently unreproducible and variable depending on the composition of the complex liquid applied to the sensing surface. However, it is apparent from FIG. 2B that, after an equilibration period, the change in dissipation due to non-specific binding in the negative sample is low whereas there is a clear change in the dissipation due to the binding of the target nucleic acid to the sensing surface.

Figure 3A:
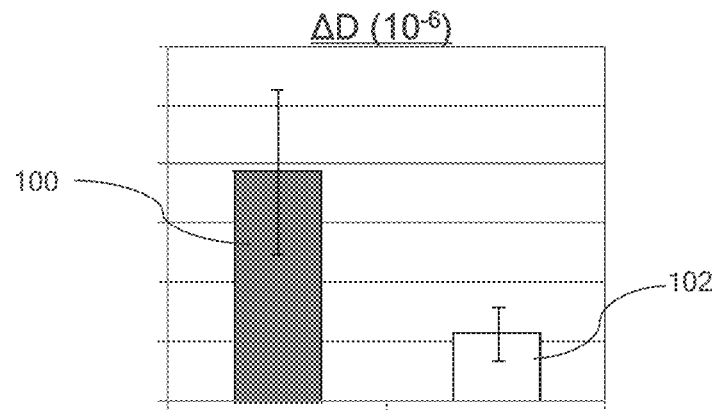
FIGS. 3A, 3B and 3C shows the changes in dissipation (D) (FIG. 3A) frequency (F) (FIG. 3B) and acoustic ratio (ΔD/ΔF) (FIG. 3C) between the positive (grey bars corresponding to 100) and negative (white bars corresponding to 102) samples (5 repeats), obtained with a QCM device and the surfaces shown in FIGS. 1A and 1B. Better discrimination between positive and negative samples can occur through dissipation measurement.
Figure 3B:
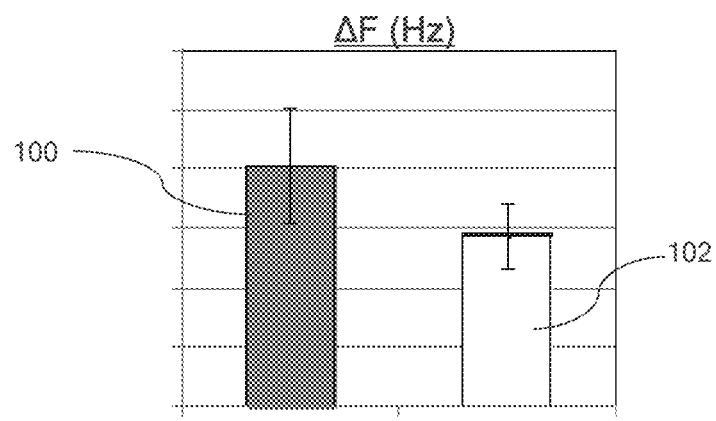
Figure 3C:
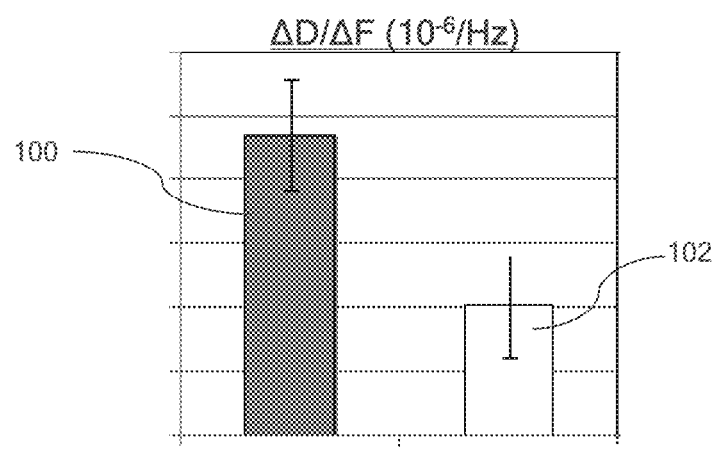

Furthermore, FIGS. 3A through 3C show average results from five experiments similar to the one described above and shown in FIGS. 2A and 2B; indeed, a measurement of the change in dissipation ($\Delta D$) clearly distinguishes the positive sample from the negative sample, but a measurement of the change in frequency ($\Delta F$) is not reliable (large error bars) due to a strong signal arising from the mass of non-analyte material in the complex sample binding non-specifically to the sensing surface. With reference to FIG. 3C, a measurement of the acoustic ratio ($\Delta D/\Delta F$) is slightly better than a measure of the change in frequency ($\Delta F$) alone but, surprisingly, a measurement of the change in dissipation ($\Delta D$) alone gives the most reliable measurement of the presence or absence of the analyte, in an impure sample.

Second Validation on a Love Wave Device

Experiments were also carried out using a Love wave surface acoustic wave-based (SAW) sensor. The SAW sensor surface was covered with a PLL-PEG copolymer as set out above and cleaned by air plasma etching.

*Salmonella* cells isolated from milk or LB growth medium were lysed with Triton-X 100 and a genomic DNA region was amplified at 63° C. using the LAMP method. The amplification reaction was diluted 5× and loaded directly on the SAW surface covered with the PLL-PEG copolymer.

FIGS. 7A through 7C show corresponding measurements of the change in amplitude, phase and the acoustic ratio for a sample of lysed whole *Salmonella* cells together with the LAMP reagents, with (positive) and without (negative) the target nucleic acid. Both positive data shown are in milk but represent measurements carried out by a different person. Again, it can be seen that the change in amplitude, which is related to energy dissipation, is more reliable than the change in phase or the acoustic ratio.

Example 2—Specific Binding

Figures 4A, 4B:
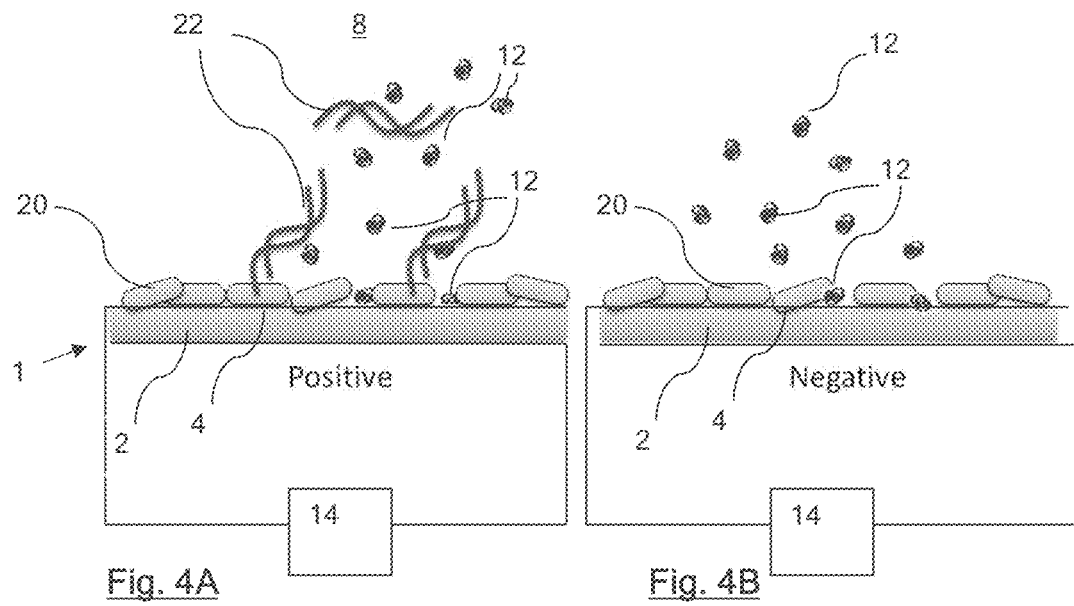
FIG. 4A is a schematic representation of a nucleic acid probe binding to an acoustic sensor sensing surface by virtue of specific interaction between neutravidin and biotin, along with some non-specific binding components.
FIG. 4B is a schematic representation of a corresponding negative.

In an alternative embodiment, shown in FIGS. 4A and 4B, the gold surface 4 of a QCM sensor has a neutravidin layer 20 formed thereon. Neutravidin (deglycosylated avidin, Neutravidin is a trade mark) adheres directly to a gold surface. Formation of neutravidin layers is well understood by those skilled in the art.

An analyte NA (where present) may be amplified using an amplification procedure (e.g. PCR, LAMP, HDA, RCA) but the product NA includes a biotin moiety towards one end (for example, by using biotinylated primers in a nucleic acid amplification step).

The product of the amplification reaction, sample liquid 8, is brought into contact with the sensing surface. The sample liquid includes target nucleic acid 22 (where present in a positive sample) as well as other components 12 as before. In this case, the sample liquid includes unused reagents and by-products of the amplification reaction.

The biotin in the target NA (where present) binds specifically to the neutravidin through one or several specific points, and so the DNA is adhered to the sensing surface, extending away from the sensing surface, typically at a defined orientation. We have found that this has a substantial effect on the energy loss of the acoustic wave generated by the device 14 while other components (22) bind tightly to the device surface and have little effect on the energy loss of the acoustic wave but do significantly alter the mass-related signal of the acoustic wave and so the ratio of the change in energy loss to the change in frequency or phase.

Thus, this configuration also provides a suitable arrangement to reliably detect a target nucleic acid using a measurement related to the change in the energy loss of an acoustic wave produced by the acoustic wave sensor.

Experimental Results of Example 2: Specific Binding

Validation on a QCM

Experiments to validate the second example embodiment were carried out as follows:

In another example (FIG. 5), the impure sample is whole blood containing both the target DNA, here *Salmonella* amplified to have a biotin at one end (22) during Lamp amplification, and other components (12) such as the Lamp reagents and by-products and other non-specific DNA molecules and proteins present in the blood sample. The biotinylated NA *Salmonella* amplification products were detected after loading the impure LAMP amplification mixture on the surface of a device coated with neutravidin, to which biotin specifically binds.

0, 50 or 1000 bacteria were spiked into 2.5 µl of whole blood (with anticoagulant) and then mixed with LAMP reagents containing one biotinylated primer. A LAMP reaction took place for 30 min and the products of the reaction was loaded on a QCM gold crystal covered with Neutravidin (Neutravidin is a trade mark of Pierce Biotechnology, Inc.).

Figure 5A:
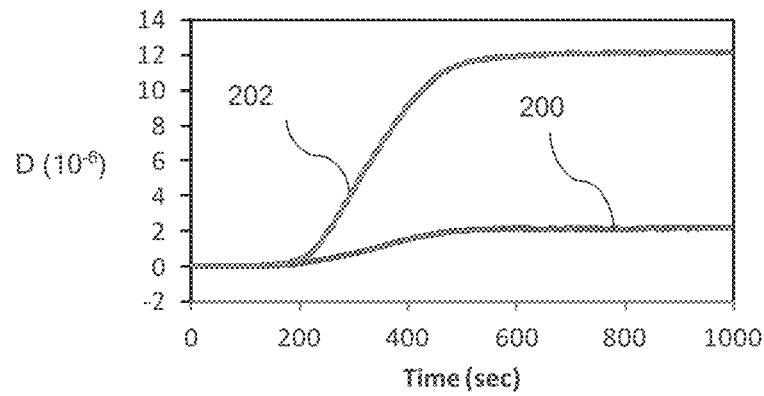
FIGS. 5A and 5B represent dissipation (FIG. 5A) and frequency change (FIG. 5B) during the binding of biotinylated target NA to a neutravidin-modified QCM acoustic device surface illustrated in FIGS. 4A and 4B, in the presence of a positive sample (202) and a negative sample (200).
Figure 5B:
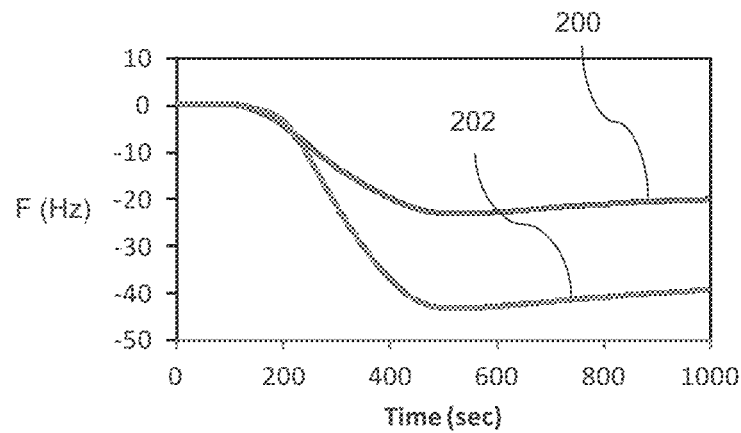
Figure 6A:
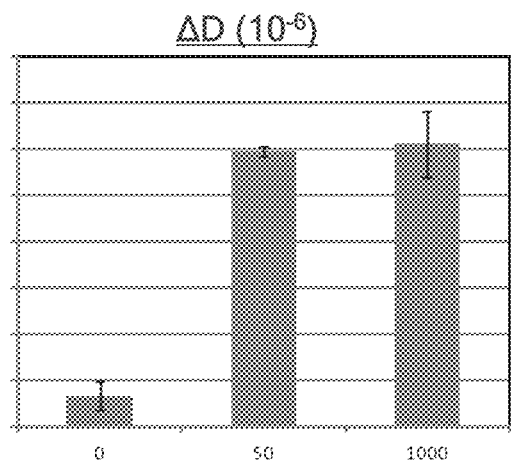
FIGS. 6A, 6B and 6C show the changes in dissipation (D) (FIG. 6A), frequency (F) (FIG. 6B) and acoustic ratio (ΔD/ΔF) (FIG. 6C) between positive (50 and 1000 cells in the initial sample) (202) and negative (0 cells in the initial sample) (200) samples (5 repeats each), obtained with the QCM device and the surfaces shown in FIGS. 4A and 4B. A much better discrimination capability is illustrated through dissipation (and here acoustic ratio) measurements.
Figure 6B:
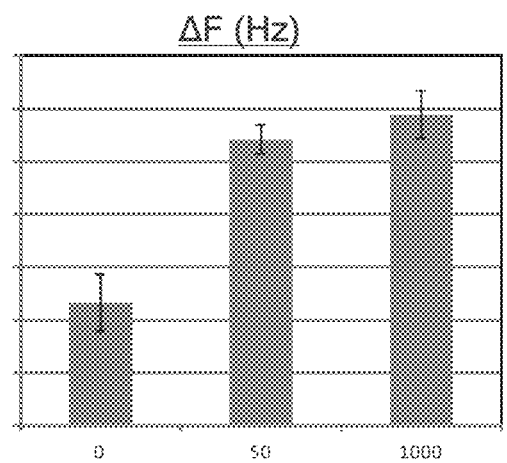
Figure 6C:
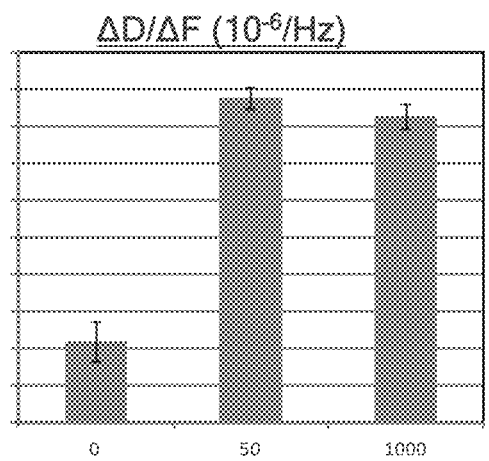
Figure 8A:
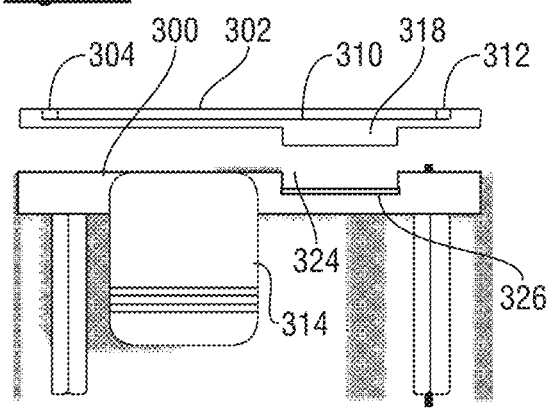
FIGS. 8A, 8B, 8C, and 8D are schematic diagrams of sensing apparatus with integrated nucleic acid amplification and acoustic detection, useful with either the implementation of FIGS. 1A and 1B or the implementation of FIGS. 4A and 4B.
Figure 8B:
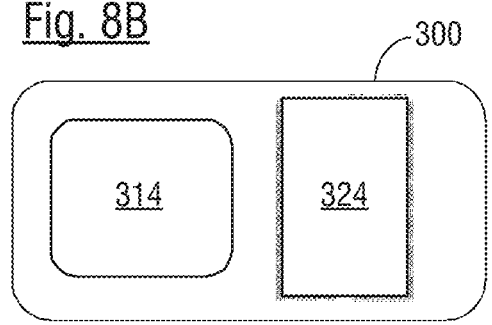
Figure 8C:
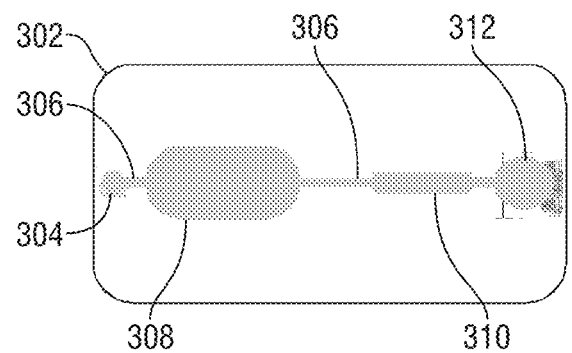
Figure 8D:
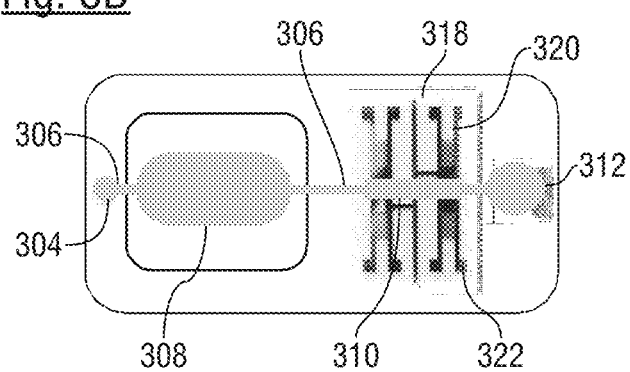

FIGS. 5A and 5B show the real-time change in dissipation and frequency for the reactions with 0 and 50 cells respectively. The experiment with 0 cells is labelled 200 (negative) and the experiment with 50 cells is labelled 202 (positive). FIGS. 6A to 6C summarize corresponding measurements of changes in dissipation, frequency and acoustic ratio.

It can be seen from FIGS. 6A through 6C, where the average changes over 5 experiments are presented, the change in dissipation provides a useful and reliable measurement with which to detect the presence of target NA.

In some embodiments, the NA has multiple specific binding moieties, for example it may be multi-biotinylated, and so typically binds the surface with multiple specific bonds.

EXPERIMENTAL DETAILS

Materials $H_2O_2$, $H_2SO_4$, Tris(hydroxymethyl)aminomethane hydrochloride (TRIS HCl), Phosphate buffered saline; 10 mM phosphate buffer; 138 mM NaCl; 2.7 mM KCl (PBS, P4417), PLL(225) and fetal bovine serum (FBS) were purchased from Sigma-Aldrich/Merck KGaA (Darmstadt, Germany). PLL(25)-g-PEG(2) and PLL(25)-g-PEG(5) were purchased from Nanocs Inc. (PG2K-PLY and PGSK-PLY, New York, U.S.A.). QCM gold sensors were purchased from Biolin Scientific (QSX301, Stockholm, Sweden). Nucleospin Gel and PCR clean-up kit (Macherey-Nagel, Germany). DNA primers 100 μM (Metabion, Germany). λPstI ladder (Minotech, Greece). NeutrAvidin Biotin-binding Protein (ThermoFisher, U.S.A.). Bst 3.0 DNA polymerase (NEB, U.S.A.). *Salmonella* Typhymurium cells were kindly provided by Institut Pasteur (Paris, France). UHT milk was used as a model real complex sample (milk consists of 3.5% fat, 3.5% proteins, 5% lactose (carbohydrate) and $10^4$ to $10^5$ somatic cells per mL). Luria-Bertani (LB) a nutrient-rich microbial broth that contains peptides, amino acids, water-soluble vitamins, and carbohydrates was prepared by mixing 10 g/L Tryptone, 5 g/L Yeast Extract and 5 g/L NaCl. Whole blood from a healthy donor was provided by the General University Hospital of Heraklion in a standard tube containing EDTA anticoagulant.

Methods

1. Experimental Setup of Acoustic Measurements 1.1. QCM-D Measurements:

Gold sensors were cleaned with piranha solution prepared in situ, adding 4 drops $H_2SO_4$ (95-97%) and 2 drops $H_2O_2$ (30%) on a gold surface. The surface was then rinsed with $H_2O$ and dried under a stream of nitrogen gas. All the experiments were carried out in buffer solution. Resonance frequency ($\Delta F$) and energy dissipation ($\Delta D$) changes were measured using a Q-Sense E4 QCM-D sensor (Biolin Scientific, Stockholm, Sweden) at operating frequency of 5 MHz and its overtones, with continuous a flow rate of 50 μL/min at 25° C. PLL (25)-g-PEG (2) and PLL (25)-g-PEG (5), as well as PLL (225) films were formed on the clean gold-coated QCM surface by applying a solution of 0.1 mg/ml in PBS or Tris buffer on the device surface; PLL films were formed by applying a solution of 0.01% (w/v) in Tris or PBS. All results reported in this study regard the $7^{th}$ harmonic overtone i.e. 35 MHz and the frequency is not divided by the overtone number.

1.2: SAW Measurements:

Surface Acoustic Wave devices (SAW) operating at 155 MHz were prepared by photolithography. These devices were used to support a Love wave in a configuration employing a photoresist S1805 (Rohm and Haas, USA) waveguide layer of 1 μm thickness. A Network analyzer (E5061A, Agilent Technologies, USA) and a LabVIEWsoftware (National Instruments, Austin, Tex.) were used for signal generation/detection and real-time monitoring of the acoustic signal. Prior to use, the polymer coated device surface was cleaned by air plasma etching (PDC-002, Harrick) for 150 s.

2. DNA Amplification from Whole *Salmonella* Cells 2.1 PCR Reactions:

DNA amplicons were produced from 1 μL of *Salmonella* Typhimurium cells (provided by Pasteur Institute, Paris, France) added in various concentrations in the PCR reactions using the Hotstart polymerase kit (KAPA Biosystems Inc., Wilmington, Mass., USA) and following the manufacturer instructions. 10 pmoles of each of the forward and reverse primers were included in each amplification reaction. The reactions were conducted with a PeqStar 2x (Peqlab Biotechnologie GmbH, Erlangen, Germany) thermocycler at 95° C. for 3 min, followed by 40 cycles of 95° C. for 10 sec, 62.5° C. for 10 sec and 72° C. for 10 sec. The final step was at 72° C. for 1 min. Primers were used for the 635 bp DNA and for the 195 bp fragment.

For the direct amplification from milk samples UHT whole milk was diluted 10 times (according to EU regulation) in LB growth medium and then spiked with *Salmonella* cells to a final concentration of $10^3$ CFU/μL. 1 μL of the complex sample was added in the PCR mix (25 μL in total) along with 1.5 μL of $MgCl_2$ (25 mM) that was required to compensate for the PCR inhibitory effect of high calcium present in the milk sample.

2.2 LAMP Reactions:

DNA amplicons were produced from 1 μL of *Salmonella* Typhimurium cells added in various concentrations in the LAMP reactions using the Bst 3 polymerase. *Salmonella* cells were lysed for 10 min with 0.1% Triton-X 100. The reactions were conducted at 63° C. for 15-30 min. Six (6) primers were used.

The amplification mix contained the following:

5.25 ul $H_2O$, 2.5 μL Isothermal Amplification Buffer II, 1.5 μL MgSO4 100 mM, 3 μL dNTPs 10 mM each, 0.25 μL F3 10 uM, 0.25 μL B3 10 uM, 4.5 μL FIP 10 uM, 4.5 μL BIP 10 uM, 1 μL LoopF 10 uM, 1 μL LoopB 10 uM, 0.25 μL Bst 3.0 Polymerase For the direct amplification from whole blood, 2.5 μL of blood was spiked with *Salmonella* cells and added in the LAMP reaction.

Integrated Amplification and Detection Apparatus

One skilled in the art will appreciate that there are numerous ways in which the liquid sample may be brought into contact with the sensing surface.

In one example, shown in FIGS. 8A through 8D, an integrated amplification and detection device comprises a base 300 into which fits a disposable plastics cassette 302. The disposable plastics cassette comprises an inlet 304 and a channel 306 which extends from the inlet through an amplification chamber 308 to an acoustic detection region 310 and thereby to an outlet 312.

The chassis retains a heating element (resistive heater or peltier) 314 in thermal communication with the amplification chamber of a disposable cassette, when present. A temperature controller (not shown) regulates the temperature in the amplification chamber. An acoustic sensor 318 having electrodes 320, 322 is formed on the underside of the acoustic detection region 310 of the cassette, but with the sensing surface in contact with the interior of the acoustic detection region. The base 300 has a recess 324 for receiving the acoustic sensor, with electrical contacts 326 which connect to electrical contacts of the acoustic sensor, to drive the acoustic sensor and measure properties of the acoustic wave.

In use, a fresh cassette is fitted into the base. Buffer fills the cassette. A crude sample for analysis (e.g. a sample of patient tissue, blood, urine etc.) is mixed with amplification reagents and introduced into the inlet. The heating element and temperature controller are used to control the temperature in the amplification chamber as is known in the art while an amplification reaction takes place. The amplification reaction produces a target nucleic acid in large amounts if an analyte (which may or may not be the target nucleic acid) is present in the received crude sample. The liquid product of the amplification reaction is then drawn or pushed through the channel into the acoustic detection region by a pump or with a pipette, without an intermediate filter or another purification step. Material in the liquid product of the amplification reaction then adheres to the sensing surface. The acoustic sensor measures the dissipation of energy by the sensing surface once the liquid product is present and a processor determines the presence and optionally amount of nucleic acid analyte which is present.

In a still further alternative embodiment, a single chamber in a disposable cassette includes both the amplification and acoustic detection regions. In that case, amplification and acoustic detection can be carried out in the same chamber, at the same time. The temperature in the chamber is varied according to the requirements of the amplification procedure (e.g. kept constant in the case of an isothermal procedure, or cycled in the case of PCT etc.).

Further modifications and variations may be made within the scope of the invention herein disclosed.

The invention claimed is:

1. A method of measuring a nucleic acid target in an impure liquid sample, the method comprising:
   providing an acoustic wave sensor having a sensing surface;
   applying the acoustic wave sensor to the impure liquid sample;
   generating an acoustic wave in the impure liquid sample through the sensing surface while the impure liquid sample is in contact with the sensing surface;
   measuring the energy loss of the acoustic wave; and
   comparing the measured energy loss with a reference to thereby determine the presence of the nucleic acid target,
   in which changes in the frequency of the acoustic waves arising from the adherence of the nucleic acid target and/or non-target nucleic acids and/or biological molecules and/or cell fragments and/or (added) reagents are not monitored by virtue of measurements of acoustic wave frequency or phase or velocity,
   wherein the impure liquid sample in contact with the sensing surface comprises at least one of:
   i. a crude sample;
   ii. a sample comprising whole or lysed cells; and
   iii. reagents for procedures carried out before detection with the acoustic sensor.

2. A method according to claim 1, wherein the reference is the measured energy loss before the impure liquid sample is brought into contact with the sensing surface.

3. A method according to claim 1, wherein the reference is a predetermined stored value or a measured energy loss of a control.

4. A method according to claim 1, wherein the impure liquid sample comprises biological molecules and/or cell fragments, at least some of which adhere to the sensing surface.

5. A method according to claim 1, wherein the impure liquid sample brought into contact with the sensing surface comprises reagents of a nucleic acid amplification procedure, at least some of which adhere to the sensing surface.

6. A method according to claim 5, wherein the nucleic acid amplification procedure is carried out on a crude initial sample, the crude initial sample comprising biological molecules and/or cell fragments, and wherein the crude liquid sample which is brought into contact with the sensing surface comprises biological molecules and/or cell fragments from the crude initial sample, at least some of which adhere to the sensing surface.

7. A method according to claim 5, wherein the nucleic acid amplification procedure is carried out in an amplification chamber which is connected to the acoustic wave sensor and the method comprises transferring product of the amplification procedure as the impure liquid sample to the sensing surface through a channel.

8. A method according to claim 7, wherein the amplification chamber and the channel are formed as an integral unit.

9. A method according to claim 7, wherein the amplification chamber is brought into thermal communication with a heater and the temperature within the amplification chamber is regulated.

10. A method according to claim 7, wherein the transfer of product of the amplification procedure is effected by a peristaltic pump, syringe pump, gravity or capillary forces.

11. A method according to claim 5, wherein the nucleic acid amplification procedure is carried out in an amplification chamber which is defined in part by the sensing surface.

12. A method according to claim 11, wherein the nucleic acid amplification procedure and the detection of the nucleic acid at the sensing surface are carried out concurrently.

13. A method according to claim 1, wherein the impure liquid sample is a crude sample extracted from a patient, or a food sample, or an environmental sample.

14. A method according to claim 1, wherein the nucleic acid target is formed in the presence of an analyte by a nucleic acid amplification procedure, and the nucleic acid target includes a first specific recognition molecule, and wherein the sensing surface comprises a second specific recognition molecule which binds specifically to the first specific recognition molecule in the presence of the impure liquid sample.

15. A method according to claim 1, wherein the nucleic acid target adheres to the sensing surface in a non-specific manner that is independent of the nucleotide sequence of the nucleic acid target.

16. A method according to claim 1, wherein the nucleic acid target in a crude initial sample adheres electrostatically to the sensing surface, changing the energy of the acoustic wave.

17. A method according to claim 1, wherein the sensing surface has a cationic layer thereon to which the nucleic acid target adheres, changing the energy of the acoustic wave.

18. A method according to claim 1, wherein biological macromolecules other than the nucleic acid target, and/or cell fragments and/or (added) reagents, adhere to the sensing surface, either without affecting the energy of the wave or affecting the energy significantly less than the adhered nucleic acid analyte.

19. A method according to claim 18, wherein the mass of biological macromolecules other than the nucleic acid target, and/or cell fragments and/or (added) reagents which adheres to the sensing surface may be greater than 20%, or greater than 50% of the mass of the nucleic acid target which adheres to the sensing surface.

* * * * *